United States Patent
Schultz et al.

(10) Patent No.: US 8,658,402 B2
(45) Date of Patent: Feb. 25, 2014

(54) PROCESS FOR THE PRODUCTION OF ESTERS

(75) Inventors: Michael Anthony Schultz, Roselle, IL (US); Derek Wayne Griffin, Roselle, IL (US)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 13/477,827

(22) Filed: May 22, 2012

(65) Prior Publication Data

US 2012/0301934 A1    Nov. 29, 2012

Related U.S. Application Data

(60) Provisional application No. 61/489,090, filed on May 23, 2011.

(51) Int. Cl.
  *C12P 7/62* (2006.01)
(52) U.S. Cl.
  CPC ................................. *C12P 7/625* (2013.01)
  USPC ........................................................ 435/135
(58) Field of Classification Search
  None
  See application file for complete search history.

(56) References Cited

U.S. PATENT DOCUMENTS

| | | | |
|---|---|---|---|
| 5,000,925 A * | 3/1991 | Krishnamurthy et al. | 48/61 |
| 5,173,429 A | 12/1992 | Gaddy et al. | |
| 5,593,886 A | 1/1997 | Gaddy | |
| 5,625,094 A | 4/1997 | Nobel et al. | |
| 5,807,722 A | 9/1998 | Gaddy | |
| 5,821,111 A | 10/1998 | Gaddy | |
| 6,136,577 A | 10/2000 | Gaddy | |
| 6,340,581 B1 | 1/2002 | Gaddy | |
| 6,368,819 B1 | 4/2002 | Gaddy et al. | |
| 6,809,217 B1 | 10/2004 | Colley et al. | |
| 2009/0005588 A1 | 1/2009 | Hassan et al. | |
| 2010/0029980 A1 | 2/2010 | Johnston et al. | |

FOREIGN PATENT DOCUMENTS

| | | |
|---|---|---|
| EP | 107496 B1 | 2/1984 |
| EP | 117309 | 9/1984 |
| EP | 131998 B1 | 1/1985 |
| EP | 104197 B1 | 5/1986 |
| NZ | WO 2007/117157 | 10/2007 |
| NZ | WO 2008/115080 | 9/2008 |
| WO | WO 98/00558 | 1/1998 |
| WO | WO 0020375 A1 * | 4/2000 |
| WO | WO 00/68407 | 11/2000 |
| WO | WO 2009003054 A1 * | 12/2008 |
| WO | WO 2009064200 A2 * | 5/2009 |

OTHER PUBLICATIONS

Demler, M., Weuster-Botz, "Reaction Engineering Analysis of Hydrogenotrophic Production of Acetic Acid by Acetobacterum Woodii", Biotechnology and Bioengineering, vol. 108, No. 2, Feb. 2011.
*Clostridium carboxydivorans* (Liou et al., International Journal of Systematic and Evolutionary Microbiology 33: pp. 2085-2091), May 27, 2005.
Abrini (*Clostridium autoethanogenum*, sp. Nov., An Anaerobic Bacterium That Produces Ethanol From Carbon Monoxide; Arch. Microbiol., 161: 345-351 (1994)).
C. Plata et al. Formation of ethyl acetate and isoamyl acetate by various species of wine yeasts. Food Microbiology. 2003, vol. 20, No. 2, pp. 217-224.
David W Armstrong et al. Production of Ethyl Acetate from Dilute Ethanol Solutions by *Candida utilis*. Biotechnology and Bioengineering. 1984, vol. 26, No. 9, pp. 1038-1041.

* cited by examiner

*Primary Examiner* — David J Steadman
*Assistant Examiner* — Paul Holland
(74) *Attorney, Agent, or Firm* — Frank S Molinaro

(57) ABSTRACT

Methods for producing an ester from a gas comprising carbon monoxide. More specifically the invention provides for methods for producing one or more products by the anaerobic fermentation of a gaseous substrate comprising CO and the subsequent conversion of the one or more products to an ester in a down-stream reaction. The invention further provides methods for improving the efficiency of the production of esters from gaseous substrates.

5 Claims, 4 Drawing Sheets

PROCESS FOR THE PRODUCTION OF ESTERS

FIELD OF THE INVENTION

The present invention relates to the production of one or more chemical products utilising a step involving microbial fermentation, particularly microbial fermentation of substrates comprising CO. In particular the invention relates to the production of one or more fermentation products, and a further reaction step for converting one or more fermentation products to an Ester.

BACKGROUND OF THE INVENTION

Ethyl Acetate also referred to as ethyl ethanoate is an ester derived from the combination of ethanol and acetic acid. Ethyl acetate is manufactured on a large scale for use as a solvent, such as for nail polish and nail polish removers, as an activator in paints, and can be used in the decaffeination of coffee and tea.

Ethyl acetate is synthesised industrially via the Fischer esterification reaction of ethanol and acetate, said reaction having the following stoichiometry:

$$CH_3CH_2OH + CH_3COOH \leftrightarrows CH_3COOCH_2CH_3 + H_2O$$

Another method for the industrial production of ethyl acetate is the catalytic dehydrogenation of ethanol. Typically dehydrogenation is conducted with copper at an elevated temperature. This method for the production of ethyl acetate is less cost effective than the Fischer esterification reaction, but can be applied in chemical plants with surplus ethanol.

Carbon Monoxide (CO) is a major by-product of the incomplete combustion of organic materials such as coal or oil and oil derived products. Although the complete combustion of carbon containing precursors yields CO2 and water as the only end products, some industrial processes need elevated temperatures favoring the build up of carbon monoxide over CO2. One example is the steel industry, where high temperatures are needed to generate desired steel qualities. For example, the steel industry in Australia is reported to produce and release into the atmosphere over 500,000 tonnes of CO annually.

Furthermore, CO is also a major component of syngas, where varying amounts of CO and H2 are generated by gasification of a carbon-containing fuel. For example, syngas may be produced by cracking the organic biomass of waste woods and timber to generate precursors for the production of fuels and more complex chemicals.

The release of CO into the atmosphere may have significant environmental impact. In addition, emissions taxes may be required to be paid, increasing costs to industrial plants. Since CO is a reactive energy rich molecule, it can be used as a precursor compound for the production of a variety of chemicals.

It is an object of the present invention to provide a process for the production of one or more chemical products, including processes which produce ethyl acetate that overcomes or ameliorates one or more of the disadvantages of the prior art, or to at least to provide the public with a useful choice.

SUMMARY OF THE INVENTION

In one aspect, the invention provides a method of producing one or more chemical products the method comprising at least the step of anaerobically fermenting a substrate comprising CO to produce one or more fermentation products.

In one embodiment, the invention provides a method of producing an ester from a gaseous substrate comprising CO, the method comprising;
a. passing the gaseous substrate comprising CO to a bioreactor containing a culture of one or more microorganism;
b. anaerobically fermenting the substrate comprising CO to produce a fermentation broth comprising first and second fermentation products;
c. passing the first and second fermentation products from step (b) to a reaction vessel; and
d. reacting the first and second fermentation products to produce a reaction broth comprising a third product.

In one embodiment said first and second products are an alcohol and an acid. In one embodiment the third product is an ester. In one embodiment the first and second fermentation products are an alcohol and an acid. In on embodiment the alcohol and acid are extracted from the fermentation broth prior to being added to the reaction vessel. In certain embodiments the first and second fermentation products are ethanol and acetic acid, and the third product is ethyl acetate.

According to one embodiment the substrate comprising CO is gaseous. In certain embodiments the substrate comprising CO contains $H_2$ or $CO_2$ or mixtures thereof. In certain embodiments the substrate comprising CO is derived from an industrial process.

In one embodiment, the reaction between the first and second fermentation products is an esterification reaction. In certain embodiments the ester is distilled from the reaction broth to provide an ester stream, and a waste stream. In certain embodiments the waste stream is returned to the bioreactor. In certain embodiments the waste stream is treated prior to being passed back to the bioreactor. In certain embodiments the treated stream being passed back to the bioreactor is substantially water.

In accordance with particular embodiments the production of an ester from a gaseous substrate comprising CO is a continuous process.

According to a second aspect, the invention provides a method for the production of ethyl acetate from a gaseous substrate comprising CO, the method comprising;
a. anaerobically fermenting a substrate comprising CO to produce ethanol;
b. adding the ethanol of step a) to a reaction vessel comprising acetic acid; and
c. reacting the ethanol and acetic acid together to produce ethyl acetate.

In a third aspect, the invention provides a method of producing one or more chemical products the method comprising at least the steps of anaerobically fermenting a gaseous substrate comprising a carbon source to produce a first product; anaerobically fermenting a second gaseous substrate comprising a carbon source to produce a second product; and reacting said first and second products together to produce a third product.

In one embodiment, the invention provides a method for the production of an ester, the method comprising:
a. providing a gaseous substrate comprising CO to a first bioreactor containing a culture of one or more microorganisms;
b. anaerobically fermenting the substrate comprising CO to produce one or more alcohols;
c. providing a gaseous substrate comprising $CO_2$ and $H_2$ to a second bioreactor containing a culture of one or more microorganisms;
d. anaerobically fermenting the gaseous substrate comprising $CO_2$ and $H_2$ to produce one or more acids;

e. flowing the one or more alcohols from the first bioreactor to a reaction vessel;

f. flowing the one or more acids from the second bioreactor to the reaction vessel; and g. reacting the one or more alcohols with the one or more acids to produce one or more esters.

In one embodiment the one or more alcohols is ethanol, and the one or more acids is acetic acid. In one embodiment the one or more esters is ethyl acetate.

In a fourth aspect, the invention provides a method for the production of one or more products from an industrial gas stream, the method comprising;

a. passing a hydrocarbon rich gas stream into a Steam Methane Reformer to produce a gaseous stream comprising at least CO and $H_2$;

b. passing the gaseous stream from step a into a Water Gas Shift Reactor, wherein at least a portion of the gas stream undergoes a water gas shift reaction to provide a substrate comprising CO, $CO_2$ and $H_2$;

c. passing the substrate from step b through a Pressure Swing Adsorption stage, wherein at least a portion of the Hydrogen is separated from the substrate;

d. passing the hydrogen depleted substrate through a second PSA stage wherein the substrate from step c is separated into a CO rich substrate, and a $CO_2$ rich substrate;

e. flowing the CO rich substrate to a first bioreactor containing a culture of one or more microorganisms;

f. anaerobically fermenting the CO rich substrate to produce one or more alcohol(s);

g. flowing the $CO_2$ rich substrate to a second bioreactor containing a culture of one or more microorganisms;

h. anaerobically fermenting the $CO_2$ rich substrate to produce one or more acid(s);

i. reacting at least one of the one or more alcohols with at least one of the one or more acids to produce one or more esters.

In one embodiment, the one or more alcohol(s) is ethanol, and the one or more acid(s) is acetic acid. In one embodiment the one or more esters is ethyl acetate.

In one embodiment, additional hydrogen is added the second bioreactor to optimise the $CO_2:H_2$ ratio.

In another aspect, the invention provides a method of producing one or more esters from a gaseous substrate comprising CO, the method comprising;

a. providing the substrate comprising CO to a bioreactor containing one or more microorganisms;

b. fermenting the substrate to produce a fermentation broth comprising ethanol;

c. separating the ethanol from the fermentation broth;

d. dehydrogenating ethanol to produce ethyl acetate.

In one embodiment the dehydrogenation step produces hydrogen as a by-product of the reaction. In one embodiment the hydrogen produces is passed to the bioreactor to be used as a co-substrate in the fermentation reaction.

Although the invention is broadly as defined above, it is not limited thereto and also includes embodiments of which the following description provides examples.

BRIEF DESCRIPTION OF THE DRAWINGS

The invention will now be described in more detail and with reference to the accompanying figures, in which.

DETAILED DESCRIPTION OF THE INVENTION

Figure 1:
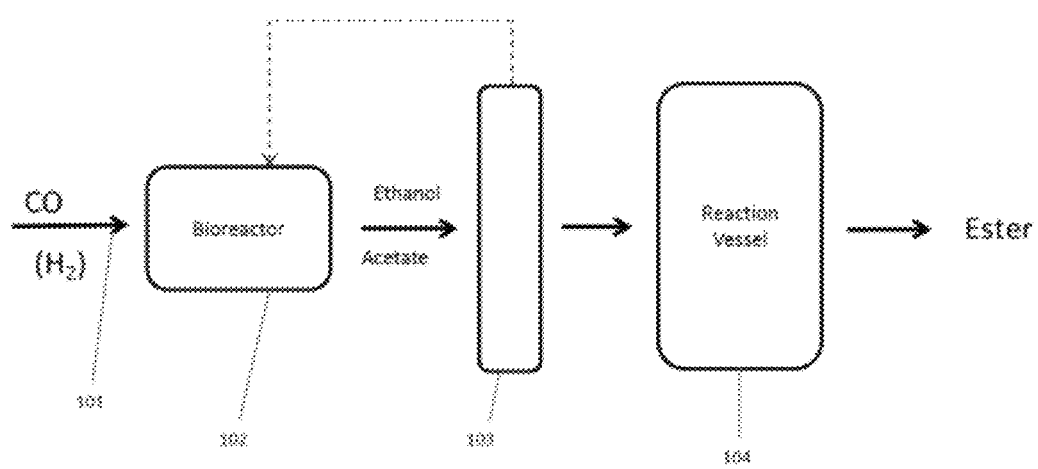
FIG. 1 is a schematic representation of a system and method for the production of an ester from a gaseous substrate.

The following is a description of the present invention, including preferred embodiments thereof, given in general terms. The invention is further exemplified in the disclosure given under the heading "Examples" herein below, which provides experimental data supporting the invention, specific examples of aspects of the invention, and means of performing the invention.

DEFINITIONS

Unless otherwise defined, the following terms as used throughout this specification are defined as follows:

The term "substrate comprising carbon monoxide and/or hydrogen" and like terms should be understood to include any substrate in which carbon monoxide and/or hydrogen is available to one or more strains of bacteria for growth and/or fermentation, for example.

"Gaseous substrate comprising carbon monoxide and/or hydrogen" includes any gas stream which contains carbon monoxide and/or hydrogen. The gaseous substrate may contain a significant proportion of CO, preferably at least about 2% to about 75% CO by volume and/or preferably about 0% to about 95% hydrogen by volume.

In the context of fermentation products, the term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

The term "hydrocarbon" includes any compound that includes hydrogen and carbon. The term "hydrocarbon" incorporates pure hydrocarbons comprising hydrogen and carbon, as well as impure hydrocarbons and substituted hydrocarbons. Impure hydrocarbons contain carbon and hydrogen atoms bonded to other atoms. Substituted hydrocarbons are formed by replacing at least one hydrogen atom with an atom of another element. The term "hydrocarbon" as used herein includes compounds comprising hydrogen and carbon, and optionally one or more other atoms. The one or more other atoms include, but are not limited to, oxygen, nitrogen and sulfur. Compounds encompassed by the term "hydrocarbon" as used herein include at least acetate/acetic acid; ethanol, propanol, butanol, 2,3-butanediol, butyrate, propionate, caproate, propylene, butadiene, isobutylene, ethylene, gasoline, jet fuel or diesel.

The term "bioreactor" includes a fermentation device consisting of one or more vessels and/or towers or piping arrangements, which includes a Continuous Stirred Tank Reactor (CSTR), Immobilized Cell Reactor (ICR), Trickle Bed Reactor (TBR), Bubble Column, Gas Lift Fermenter, Membrane Reactor such as a Hollow Fibre Membrane Bioreactor (HFMBR), Static Mixer, or other vessel or other device suitable for gas-liquid contact.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

"Fermentation broth" is defined as the culture medium in which fermentation occurs.

The term "ester" refers to any organic compound made by replacing the hydrogen of an acid by an alkyl or other organic group. In accordance with the present invention an ester is a compound formed by joining an alcohol and an acid.

The term "reactive distillation" refers to a process for the separation of a product from a reaction mixture. Reactive distillation is a technique used in equilibrium limited reactions, whereby conversion can be increased beyond what is expected by the equilibrium due to the continuous removal of reaction products from the reaction vessel.

The term "Steam reforming" is a process defined generally by the equation $$CH_4 + H_2O \rightarrow CO + 3H_2.$$

The term "Water Gas Shift" or "WGS" step refers to a process defined generally by the equation:

$$CO + H_2O \rightarrow H_2 + CO_2.$$

The term "Pressure Swing Adsorption" or "PSA" refers to a process used to recover one or more products from a gas stream.

Aspects of the invention will now be described with reference to the figures.

In accordance with one aspect of the invention a method and system of producing one or more chemical products is provided, said method comprising at least the step of anaerobically fermenting a substrate comprising CO to produce one or more products. With reference to FIG. 1 a substrate comprising CO is flowed through a gas supply conduit 101 into a bioreactor 102, said bioreactor 102 being configured for the fermentation of a substrate by a culture of one more microorganism contained in a nutrient medium. In accordance with one aspect of the invention, the substrate comprising CO i anaerobically fermented to produce a fermentation broth comprising products including at least one alcohol and at least one acid. For the purpose of describing the invention, the at least one alcohol and at least one acid will be referred to in this embodiment as ethanol and acetic acid. A skilled addressee would appreciate that any alcohol or acid combination could be produced and used in the production of an ester product in accordance with the present invention. Examples of alcohols and acids which can be used to produce esters include but are not limited to ethanol, butanol, methanol, propanol, isopropanol, isobutanol, acetic acid, butyric acid, pentanoic acid, caproic acid and succinic acid.

Examples of esters which can be produced by the methods of the present invention include but are not limited to ethyl acetate (ethyl ethanoate), ethyl propanoate, propyl ethanoate, and butyl acetate.

Referring to FIG. 1, the ethanol and acetic acid produced in the bioreactor. In preferred embodiments the ethanol and acetic acid passed to an extraction module 103, wherein the ethanol and acetic acid are each removed from the fermentation broth using suitable extraction methods, to provide substantially water free product streams. The extracted product streams are then transferred to a reaction vessel 104. The acetic acid and ethanol are reacted together to produce ethyl acetate. In certain embodiments the reaction between ethanol and acetic acid is an esterification reaction having the following stoichiometry;

$$CH_3COOH + C_2H_5OH \rightleftharpoons CH_3COOC_2H_5 + H_2O$$

The esterification reaction is an equilibrium reaction. In order to drive the reaction toward the production of ethyl acetate, water is continuously removed from the reacted product stream. The removal of water from the reacted product stream can be performed by conventional methods including reactive distillation.

Figure 2:
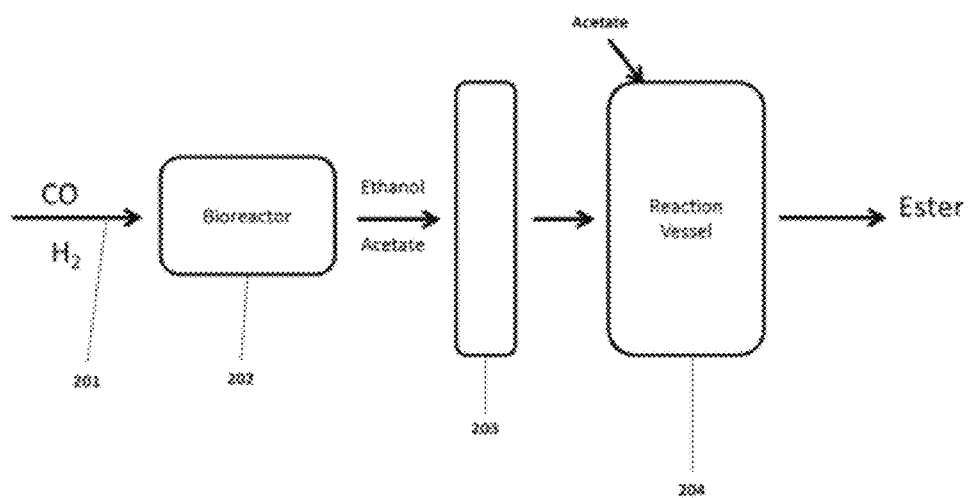
FIG. 2 is a schematic representation of a system and method in accordance with an alternative embodiment of the invention as shown in FIG. 1

In another embodiment, and with reference to FIG. 2, a gaseous substrate comprising CO is passed through the gas supply conduit 201 to a bioreactor 202. The bioreactor 202 contains a culture of one more microorganisms, and is configured to anaerobically ferment the gaseous substrate comprising CO to produce a fermentation broth comprising one or more alcohol(s). In accordance with the invention the alcohol produced by the fermentation is selected from the group comprising ethanol, butanol, propanol and isopropanol. In certain embodiments the alcohol is ethanol. The fermentation broth is passed to an extraction module 203, wherein the ethanol is extracted from the fermentation broth to provide a waste broth stream and a purified product stream. The purified product stream is passed to a reaction vessel 204. Acetic acid is added also to the reaction vessel. The ethanol and acetic acid undergoes an esterification reaction to produce ethyl acetate.

In situations where acetic acid is not available, the purified ethanol stream can be converted to ethyl acetate by the process of dehydrogenation.

Figure 3:
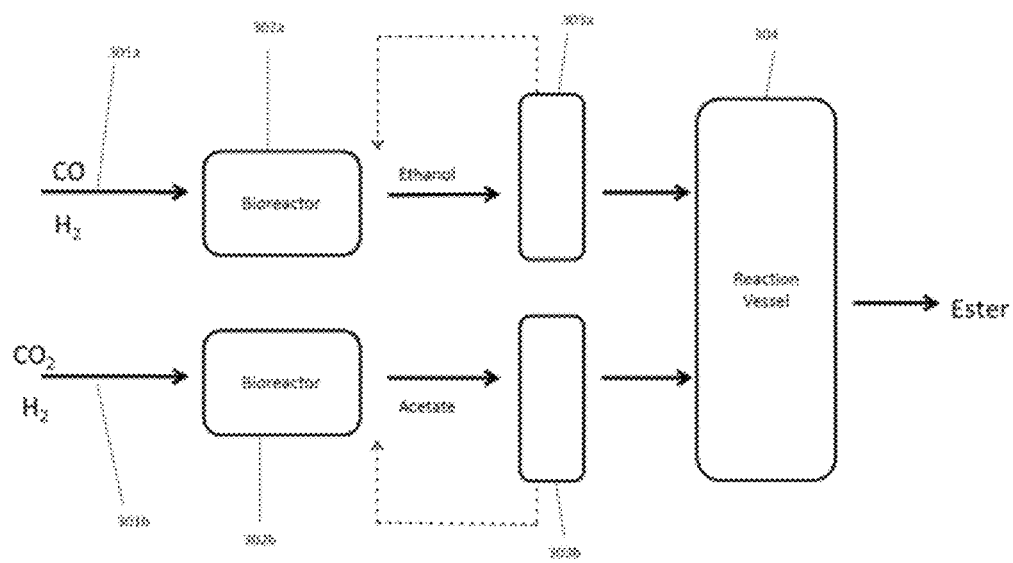
FIG. 3 is a schematic representation of a system and method showing a two fermenter system for the production of an ester from a gaseous substrate.

FIG. 3 shows an alternative embodiment of the invention, integrating two separate fermentation systems to produce an ester. Referring to FIG. 3 the system comprises a first bioreactor 302a and a second bioreactor 302b. In accordance with one aspect of the invention a first gaseous substrate comprising CO is passed to the first bioreactor 302a via a conduit 301a. The first bioreactor is configured to produce one or more alcohols (and optionally acids) by the anaerobic fermentation of the CO comprising substrate. The first bioreactor contains a culture of one or more carboxydotrophic acetogenic mircroorganisms selected from the group consisiting of *Clostridium, Moorella, Pyrococcus, Eubacterium, Desulfobacterium, Carboxydothermus, Acetogenium, Acetobacterium, Acetoanaerobium, Butyribaceterium* and *Peptostreptococcus*. More particularly the microorganism in the first bioreactor is from the group consisting of *Clostridium autoethanogenum, Clostridium ljungdahli, Clostridium ragsdalei* or *Clostridium carboxydivorans*. In certain embodiments the gaseous substrate comprising CO is fermented to produce a fermentation broth comprising ethanol. The fermentation broth is passed to an extraction module 303a, wherein the ethanol is extracted from the fermentation broth to provide a purified product stream and a waste broth stream. The purified product stream is then passed to a reaction vessel 304.

The second bioreactor 302b receives a gaseous substrate comprising CO2 and H2, said substrate being supplied via a gas supply conduit 301b. The second bioreactor 302b contains a culture of one or more microorganisms selected from the group consisting of *Moorella, Clostridium, Ruminococcus, Acetobacterium, Eubacterium, Butyribacterium, Oxobacter, Methanosarcina, Methanosarcina*, and *Desulfotomaculum*. In particular embodiments the second bioreactor contains a culture of *Acetobacterium woodii*. The gaseous substrate comprising CO2 is fermented in the second bioreactor 302b to produce a fermentation broth comprising acetic acid. The fermentation broth comprising acetic acid is passed to an extraction module 303b, wherein the acetic acid is separated from the fermentation broth to provide a purified acetic acid stream and a waste broth stream. The purified acetic acid stream is then passed to the reaction vessel 304. The purified ethanol product stream and the purified acetic acids product stream are reacted together using an esterification method to produce ethyl acetate.

Figure 4:
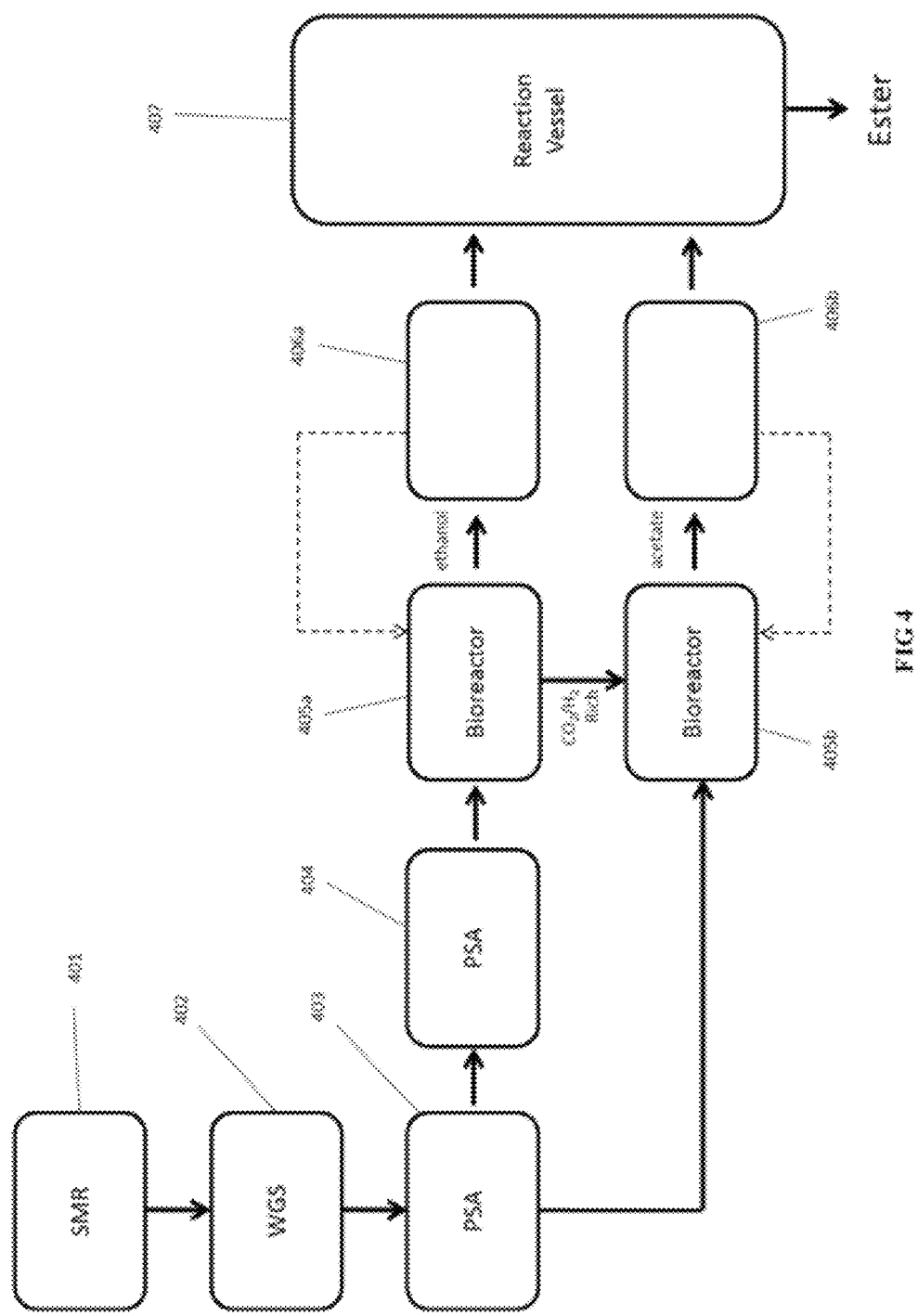
FIG. 4 is a schematic representation of a system and method for the production of an ester by fermentation of a gaseous substrate derived from an industrial process

FIG. 4 shows a system and a method wherein production of an ester is integrated to an industrial process. In accordance with one embodiment of the invention the industrial process is a steam reforming process as described herein below.

The industrial production of hydrogen using steam reforming of suitable hydrocarbon reactants (primarily methane from natural gas) generally comprises two steps—a steam reforming step and a water-gas shift step. Where methane is referred to herein, it will be appreciated by one of skill in the art that in alternative embodiments of the invention, the steam reforming process may proceed using other suitable hydrocarbon reactants, such as ethanol, methanol, propane, gasoline, autogas and diesel fuel, all of which may have differing reactant ratios and optimal conditions.

In a steam methane reformer 401, methane is reacted with steam in a molar ratio of methane:steam 3:1 in the presence of a nickel-based catalyst at a pressure of approximately 25 atm and at a temperature of approximately 700-1100° C., more preferably a temperature of approximately 800-900° C., more preferably approximately 850° C. The steam reforming reaction yields carbon monoxide and hydrogen as shown by the following equation:

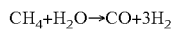

$$CH_4 + H_2O \rightarrow CO + 3H_2$$

A typical output gas composition from the steam reformer would include the following approximate composition: $H_2$—73%, $CO_2$—10%, CO—8%, $CH_4$—4%.

Secondly at least a portion of at least the CO produced in the steam reforming step is reacted with steam in the presence of a catalyst to produce hydrogen and carbon dioxide in a Water Gas Shift (WGS) vessel 402. The reaction having the following stoichiometry;

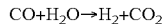

$$CO + H_2O \rightarrow H_2 + CO_2$$

The WGS reaction involves a high temperature shift (HTS) at a pressure of approximately 20-25 atm and a temperature of approximately 350-450° C. An aim of this step is to enrich the hydrogen content of the gas stream and to reduce the CO content. A typical gas composition from the WGS vessel 4 would include the following approximate composition: $H_2$—75%, $CO_2$—16%, CO—2%, $CH_4$—3%.

The WGS step is normally followed by a Pressure Swing Adsorption (PSA) step to recover the purified hydrogen stream. The gas stream from the WGS step enters a PSA reactor 403 comprising a molecular sieve system which adsorbs $CO_2$, CO, $CH_4N_2$ and $H_2O$ at high pressure. Hydrogen is able to pass through the sieve and is collected at approximately 65-90% yield (higher yield being associated with lower final $H_2$ product purity). Once saturated, the sieve is depressurised then the desorbed gases are swept out using the smallest possible quantity of hydrogen product. The extent of regeneration is a function of pressure, as a greater quantity of adsorbed species is released at lower regeneration pressures. This, in turn, leads to greater hydrogen recovery. Therefore, regeneration pressures of close to atmospheric pressure maximize hydrogen recovery. The vessel 6 is then depressurized with hydrogen ready for the next period as adsorber. Commercial systems will typically have three or four vessels to give a smooth operation. A typical gas stream output from the PSA vessel 403 would include the following: $H_2$, $CO_2$, CO and $CH_4$.

At least a portion of the gas stream exiting the PSA vessel 403 is directed to a bioreactor 405b configured to produce acid(s), said portion of the gas stream being a $CO_2$ rich stream. The remaining gas stream, typically comprising CO, $H_2$, $CH_4$ and $CO_2$ is directed to a second PSA vessel 404. The gas stream undergoes the PSA step for a second time, the resulting gas stream comprising CO, $H_2$, and $CH_4$. The gas stream exiting the second PSA vessel 404 is directed to a bioreactor 405a configured to produce alcohol(s).

The bioreactor 405a comprises one or more microorganisms from the group consisting of *Clostridium, Moorella, Pyrococcus, Eubacterium, Desulfobacterium, Carboxydothermus, Acetogenium, Acetobacterium, Acetoanaerobium, Butyribaceterium* and *Peptostreptococcus*. More particularly the microorganism in the first bioreactor is from the group consisting of *Clostridium autoethanogenum, Clostridium ljungdahli, Clostridium ragsdalei* or *Clostridium carboxydivorans*. In particular embodiments of the invention the microorganism is *Clostridium autoethanogenum*. The bioreactor 405a produces a fermentation broth comprising ethanol. The fermentation broth comprising ethanol is passed to an extraction module 406a, wherein the ethanol is separated from the fermentation broth to provide a purified ethanol stream and a waste broth stream. The purified ethanol stream is then passed to the reaction vessel 407.

This fermentation process further results in a gas stream rich in $CO_2$ and $H_2$. In one embodiment of the invention, the gas stream exiting the bioreactor 405a is directed to the bioreactor 405b.

The bioreactor 405b comprises one or more microorganisms from the group consisting of *Moorella, Clostridium, Ruminococcus, Acetobacterium, Eubacterium, Butyribacterium, Oxobacter, Methanosarcina, Methanosarcina*, and *Desulfotomaculum*. In one embodiment the microorganism in the second bioreactor is *Acetobacterium woodii*. In the second bioreactor 405b the $CO_2$ rich substrate is fermented to produce a fermentation broth comprising acetic acid. The fermentation broth comprising acetic acid is passed to an extraction module 406b, wherein the acetic acid is separated from the fermentation broth to provide a purified acetic acid stream and a waste broth stream. The purified acetic acid stream is then passed to the reaction vessel 407.

The purified ethanol stream and the purified acetic acid stream are reacted together in the reaction vessel 407 to produce ethyl acetate.

In accordance with any of the embodiments of the invention described herein it would be understood that the extracted product stream from the bioreactors will vary in acetic acid and ethanol compositions depending on the fermentation conditions in the bioreactor. A determining means can be provided for determining the ratio of ethanol to acetic acid in the reaction vessel. Additional ethanol and/or acetic acid may be added to the reaction vessel in order to optimise the ethanol to acetic acid ratio. In accordance with one embodiment of the invention the ethanol to acetic acid ratio may be 1:1 to 5:1. It would be further understood by a skilled person that additional acetic acid and or ethanol can be added to the reaction vessel to enable the production of greater amounts of ethyl acetate. The additional ethanol and or acetic acid can be derived from any suitable source. In one embodiment, the additional ethanol is derived from an industrial source.

In embodiments where ethanol is available in greater amounts to acetic acid, purified ethanol product stream can be divided, such that a first portion of the ethanol is provided to the reaction vessel to produce ethyl acetate, and a second portion of ethanol is recovered for other uses. In certain embodiments the second portion of ethanol can be directed to a second reaction vessel, wherein the ethanol undergoes a dehydrogenation reaction to produce ethyl acetate without the requirement for acetic acid. When ethanol is converted to ethyl acetate by dehydrogenation, hydrogen is produced as a by-product of the reaction. In certain embodiments the hydrogen produced in the dehydrogenation process is recovered. The recovered hydrogen can be passed to the bioreactor for use as a co substrate. Alternatively the hydrogen can be recovered for use as an energy or fuel source.

In accordance with any of the embodiments of the invention the waste broth stream produced as a by-product of the purification of ethanol and or acetic acid, can be recycled to the bioreactor. It is desirable to treat the waste broth stream to remove substances that may have a negative effect on the fermentation. In certain embodiments the waste broth stream is treated to remove biomass from the stream. The treated waste stream can then be passed into the bioreactors to meet at least part of the water and nutrient requirements of the nutrient medium required for fermentation.

In accordance with preferred embodiments of the invention the production of ethyl acetate from a gaseous substrate is a continuous product. The fermentation, extraction and reaction steps described above can all be operated in a continuous manner.

The various stages of the methods and systems outlined in the embodiments herein before will now be discussed in greater detail. It would be understood by a skilled person that the present invention is not limited by the example embodiments provided above, but can encompass any of the processes, systems or products described hereafter.

The Bioreactor

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow Fibre Membrane Bioreactor (HFM BR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor may be fed and in which most of the fermentation product (e.g. ethanol and acetate) may be produced. The bioreactor of the present invention is adapted to receive a CO and/or $H_2$ containing substrate.

The CO Containing Substrate

A substrate comprising carbon monoxide, preferably a gaseous substrate comprising carbon monoxide, is used in the fermentation reaction to produce ethanol in the methods of the invention. The gaseous substrate may be a waste gas obtained as a by-product of an industrial process, or from some other source such as from combustion engine (for example automobile) exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous substrate comprising carbon monoxide, it may also be desirable to treat it to remove any undesired impurities, such as dust particles before introducing it to the fermentation. For example, the gaseous substrate may be filtered or scrubbed using known methods.

In other embodiments of the invention, the gaseous substrate comprising carbon monoxide may be sourced from the gasification of biomass. Other materials suitable for use in the gasification process include coal and pet coke. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention. Other sources for the gaseous substrate include reforming of natural gas, including partial oxidation and $CO_2$ reforming methods.

The CO-containing substrate will typically contain a major proportion of CO, such as at least about 2% to about 75% volume or at least about 15% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

The CO containing substrate can contain hydrogen at various concentrations. Whilst the presence of hydrogen in the CO substrate is not detrimental, high hydrogen concentrations are not required for fermentation in accordance with the invention. Surprisingly it has been shown by the inventors that the substrate can comprise low concentration of $H_2$. In particular embodiments the substrate comprises $H_2$ at less than 30% or less than 20%, or less than 10% or less than 5% by volume, or less than 2% by volume. In one embodiment the substrate comprising $H_2$ contains substantially no $H_2$.

The gaseous substrate may also contain some $CO_2$ for example, such as about 1% to about 80% by volume, or 1% to about 30% by volume. In one embodiment it contains about 5% to about 10% by volume. In another embodiment the gaseous substrate contains approximately 20% $CO_2$ by volume.

Typically, the carbon monoxide will be added to the fermentation reaction in a gaseous state. However, the invention should not be considered to be limited to addition of the substrate in this state. For example, the carbon monoxide could be provided in a liquid. For example, a liquid may be saturated with a carbon monoxide containing gas and then that liquid added to a bioreactor. This may be achieved using standard methodology. By way of example, a microbubble dispersion generator (Hensirisak et. al. Scale-up of microbubble dispersion generator for aerobic fermentation; *Applied Biochemistry and Biotechnology* Volume 101, Number 3/October, 2002) could be used.

In one embodiment of the invention, a combination of two or more different substrates may be used in the fermentation reaction.

In addition, it is often desirable to increase the CO concentration of a substrate stream (or CO partial pressure in a gaseous substrate) and thus increase the efficiency of fermentation reactions where CO is a substrate. Increasing CO partial pressure in a gaseous substrate increases CO mass transfer into a fermentation media. The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

The $CO_2$ and $H_2$ Containing Substrate

Preferably the carbon source for the fermentation can be a gaseous substrate comprising carbon dioxide in combination with hydrogen. Similarly, the gaseous substrate may be a $CO_2$ and $H_2$ containing waste gas obtained as a by-product of an industrial process, or from some other source. The largest source of $CO_2$ emissions globally is from the combustion of fossil fuels such as coal, oil and gas in power plants, industrial facilities and other sources.

The gaseous substrate may be a $CO_2$ and $H_2$-containing waste gas obtained as a by-product of an industrial process, or from some another source such as from automobile exhaust fumes. In certain embodiments, the industrial process is selected from the group consisting of hydrogen manufacture, ammonia manufacture, combustion of fuels, gasification of coal, and the production of limestone and cement. The gaseous substrate may be the result of blending one or more gaseous substrates to provide a blended stream. It would be understood to a skilled person that waste gas streams rich in $H_2$ or rich in $CO_2$ are more abundant that waste gas streams rich in both $H_2$ and $CO_2$. A skilled person would understand that blending one or more gas streams comprising one of the desired components of $CO_2$ and $H_2$ would fall within the scope of the present invention.

The substrate comprising $CO_2$ and $H_2$ may comprise at least 5% $CO_2$ by volume, at least 10% $CO_2$ by volume, at least 15% $CO_2$ by volume, at least 20% $CO_2$ by volume, at least 30% $CO_2$ by volume or at least 40% $CO_2$ by volume. Substrates having higher concentration of $CO_2$, such as at least 70% by volume may also be appropriate.

The substrate comprising $CO_2$ and $H_2$ may comprise at least 30% $H_2$ by volume, at least 40% $H_2$ by volume, at least 50% $H_2$ by volume, at least 60% $H_2$ by volume, at least 70% $H_2$ by volume or at least 80% $H_2$ by volume. Substrates having lower concentrations of $H_2$ such as around 5% $H_2$ by volume, or around 10% $H_2$ by volume, or around 15% $H_2$ by volume, or around 20% $H_2$ by volume, may also be appropriate.

In certain embodiments hydrogen and carbon dioxide are provided at a ratio of approximately 1:1.

Hydrogen rich gas streams are produced by a variety of processes including steam reformation of hydrocarbons, and in particular steam reformation of natural gas. The partial oxidation of coal or hydrocarbons is also a source of hydrogen rich gas. Other sources of hydrogen rich gas include the electrolysis of water, by-products from electrolytic cells used to produce chlorine and from various refinery and chemical streams.

Gas streams typically rich in Carbon dioxide include exhaust gasses from combustion of a hydrocarbon, such as natural gas or oil. Carbon dioxide is also produced as a by-product from the production of ammonia, lime or phosphate and from natural carbon dioxide wells.

Blending of Streams

It may be desirable to blend a reformed substrate stream comprising CO and H2 with one or more further streams in order to improve efficiency, alcohol production and/or overall carbon capture of the fermentation reaction. Without wishing to be bound by theory, in some embodiments of the present invention, carboxydotrophic bacteria convert CO to ethanol according to the following:

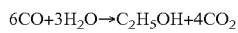

$$6CO+3H_2O \rightarrow C_2H_5OH+4CO_2$$

However, in the presence of $H_2$, the overall conversion can be as follows:

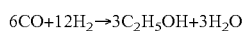

$$6CO+12H_2 \rightarrow 3C_2H_5OH+3H_2O$$

Accordingly, streams with high CO content can be blended with reformed substrate streams comprising CO and $H_2$ to increase the CO:$H_2$ ratio to optimise fermentation efficiency. By way of example, industrial waste streams, such as off-gas from a steel mill have a high CO content, but include minimal or no $H_2$. As such, it can be desirable to blend one or more streams comprising CO and $H_2$ with the waste stream comprising CO, prior to providing the blended substrate stream to the fermenter. The overall efficiency, alcohol productivity and/or overall carbon capture of the fermentation will be dependent on the stoichiometry of the CO and $H_2$ in the blended stream. However, in particular embodiments the blended stream may substantially comprise CO and H2 in the following molar ratios: 20:1, 10:1, 5:1, 3:1, 2:1, 1:1 or 1:2.

In addition, it may be desirable to provide CO and $H_2$ in particular ratios at different stages of the fermentation. For example, substrate streams with a relatively high $H_2$ content (such as 1:2 CO:$H_2$) may be provided to the fermentation stage during start up and/or phases of rapid microbial growth. However, when the growth phase slows, such that the culture is maintained at a substantially steady microbial density, the CO content may be increased (such as at least 1:1 or 2:1 or higher, wherein the $H_2$ concentration may be greater or equal to zero).

Blending of streams may also have further advantages, particularly in instances where a waste stream comprising CO is intermittent in nature. For example, an intermittent waste stream comprising CO may be blended with a substantially continuous reformed substrate stream comprising CO and $H_2$ and provided to the fermenter. In particular embodiments of the invention, the composition and flow rate of the substantially continuous blended stream may be varied in accordance with the intermittent stream in order to maintain provision of a substrate stream of substantially continuous composition and flow rate to the fermenter.

Media

It will be appreciated that for growth of the one or more microorganisms and substrate to ethanol and/or acetate fermentation to occur, in addition to the substrate, a suitable nutrient medium will need to be fed to the bioreactor. A nutrient medium will contain components, such as vitamins and minerals, sufficient to permit growth of the micro-organism used. By way of example only, anaerobic media suitable for the growth of *Clostridium autoethanogenum* are known in the art, as described for example by Abrini et al (*Clostridium*

*autoethanogenum*, sp. Nov., An Anaerobic Bacterium That Produces Ethanol From Carbon Monoxide; *Arch. Microbiol.*, 161: 345-351 (1994)). The "Examples" section herein after provides further examples of suitable media.

Fermentation

Processes for the production of ethanol and other alcohols from gaseous substrates are known. Exemplary processes include those described for example in WO2007/117157, WO2008/115080, WO2009/022925, WO2009/064200, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

Fermentation Conditions

The fermentation should desirably be carried out under appropriate conditions for the substrate to ethanol and/or acetic acid fermentation to occur. Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The optimum reaction conditions will depend partly on the particular microorganism of used. However, in general, it is preferred that the fermentation be performed at a pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-product conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-product fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

Examples of fermentation conditions suitable for anaerobic fermentation of a substrate comprising CO are detailed in WO2007/117157, WO2008/115080, WO2009/022925 and WO2009/064200. It is recognised the fermentation conditions reported therein can be readily modified in accordance with the methods of the instant invention.

Microorganisms

CO Utilising Microorganisms

In one embodiment, the parental microorganism is selected from the group of carboxydotrophic acetogenic bacteria. In certain embodiments the microorganism is selected from the group comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium coskatii*, *Butyribacterium limosum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Oxobacter pfennigii*, and *Thermoanaerobacter kiuvi*.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 23693. In another embodiment, the *Clostridium autoethanogenum* is a *Clostridium autoethanogenum* having the identifying characteristics of DSMZ deposit number DSMZ 19630, or DSMZ deposit number DSMZ 10061. These strains have a particular tolerance to changes in substrate composition, particularly of $H_2$ and CO and as such are particularly well suited for use in combination with a steam reforming process.

$CO_2$ and $H_2$ Utilising Microorganims

A number of anaerobic bacteria are known to be capable of carrying out the fermentation of $CO_2$ and $H_2$ to alcohols, including ethanol, and acetic acid, and are suitable for use in the process of the present invention. Acetogens have the ability to convert gaseous substrates such as $H_2$, $CO_2$ and CO into products including acetic acid, ethanol and other fermentation products by the Wood-Ljungdahl pathway. Examples of such bacteria that are suitable for use in the invention include those of the genus *Acetobacterium*, such as strains of *Acetobacterium woodii* ((Demler, M., Weuster-Botz, "Reaction Engineering Analysis of Hydrogenotrophic Production of Acetic Acid by *Acetobacterum Woodii*", Biotechnology and Bioengineering, Vol. 108, No. 2, February 2011) and.

*Acetobacterium woodii* has been shown to produce acetate by fermentation of gaseous substrates comprising $CO_2$ and $H_2$. Buschhorn et al. demonstrated the ability of *A. woodii* to produce ethanol in a glucose fermentation with a phosphate limitation.

Anaerobic acetogenic bacteria capable of producing acetate by feremtnation of gaseous substrates include *Acetobacterium, Moorella, Clostridium, Pyrococcus, Eubacterium, Desulfobacterium, Cabroxydothermus, Acetogenium, Acetoanaerobium, Butyribaceterium, Peptostreptococcus, Ruminococcus, Oxobacter* and *Methanosarcina*.

Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp 41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Acetobacterium woodii* having the identifying characteristics of the strain deposited at the German Resource Centre for Biological Material (DSMZ) under the identifying deposit number DSM 1030.

Methods for Culturing Microorganisms

Culturing of the bacteria used in the methods of the invention may be conducted using any number of processes known in the art for culturing and fermenting substrates using anaerobic bacteria. By way of example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

Fermentation Products

Methods of the invention can be used to produce any of a variety of hydrocarbon products. This includes alcohols, acids and/or diols. More particularly, the invention may be applicable to fermentation to produce butyric acid, propionic acid, caproic acid, ethanol, propanol, butanol, 2,3-butanediol, propylene, butadiene, isobutylene and ethylene. In one embodiment the invention can be used to produce alcohols including but not limited to propanol and butanol. The alcohol(s) can then be reacted with acetic acid to produce product(s) including propyl acetate or butyl acetate. A skilled person would understand that the invention is not limited to the alcohols and products mentioned; rather any appropriate alcohol and or acid can be used to produce a product.

The methods of the invention can also be applied to aerobic fermentations, to anaerobic or aerobic fermentations of other products, including but not limited to isopropanol. The methods of the invention can also be applied to aerobic fermentations, and to anaerobic or aerobic fermentations of other products, including but not limited to isopropanol.

The invention also provides that at least a portion of a hydrocarbon product produced by the fermentation is reused in the steam reforming process. This may be performed because hydrocarbons other than $CH_4$ are able to react with steam over a catalyst to produce $H_2$ and CO. In a particular embodiment, ethanol is recycled to be used as a feedstock for the steam reforming process. In a further embodiment, the hydrocarbon feedstock and/or product is passed through a pre-reformer prior to being used in the steam reforming process. Passing through a pre-reformer partially completes the steam reforming step of the steam reforming process which can increase the efficiency of hydrogen production and reduce the required capacity of the steam reforming furnace.

The methods of the invention can also be applied to aerobic fermentations, and to anaerobic or aerobic fermentations of other products, including but not limited to isopropanol.

More particularly, the invention may be applicable to fermentation to ethanol and/or acetate. These products may then be reacted to together to produce chemical products including esters. In one embodiment of the invention the ethanol and acetate produced by fermentation are reacted together to produce Ethyl Acetate. Ethyl acetate may be of value for a host of other processes such as the production of solvents including surface coating and thinners as well as in the manufacture of pharmaceuticals and flavours and essences. Other Esters (see list of alcohols above)

Recovery of Fermentation Products

The products of the fermentation reaction can be recovered using known methods. Exemplary methods include those described in WO07/117,157, WO08/115,080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetic acid, which may be produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented microorganisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetic acid) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetic acid have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Treatment of Biomass

Biomass recovered from the bioreactor may undergo anaerobic digestion in a digestion. to produce a biomass product, preferably methane. This biomass product may be used as a feedstock for the steam reforming process or used to produce supplemental heat to drive one or more of the reactions defined herein.

In certain aspects of the invention biomass recovered from the bioreactors of the present invention can be digested to produce a biogas comprising CO2 and CH4. In certain embodiments of the invention the CO2 can be separated from the biogas stream and passed back to the CO2/H2 fermentation process.

Conversion to Chemical Products

Ethyl acetate is used as a solvent across many industries. Ethyl acetate may be used as a solvent for surface coating and thinners and finds wide use in the manufacture of nitrocellulose lacquers, varnishes and thinners. Ethyl acetate can also be used in the concentration and purification of antibiotics as well as in the manufacture of drugs. In addition ethyl acetate is used in flavours and essences as well as in the manufacture of adhesives, cleaning fluids, inks, nail-polish removes, coated papers, explosives and photographic films and plates.

A number of know methods may be used for the production of ethyl acetate from ethanol and acetic acid. For example ethyl acetate can be obtained by esterification which is the method involving the dehydration of mixtures comprising alcohols and carboxylic acids. Common esterification methods are Fischer esterification and the Mitsunobu reaction. Another method for production of ethyl acetate is by the dehydrogenation of ethanol. This method is less cost effective than esterification but can be applied in situations where there is surplus supply of ethanol.

Production of Ethyl acetate by Fischer esterification involves treating a carboxylic acid with an alcohol in the presence of a dehydrating agent, as generally defined by the following stoichiometry;

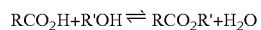
$$RCO_2H + R'OH \rightleftharpoons RCO_2R' + H_2O$$

In one embodiment of the present invention, Ethyl acetate is produced by the reaction of ethanol and acetate as shown in the following stoichiometry;

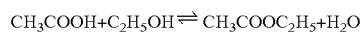
$$CH_3COOH + C_2H_5OH \rightleftharpoons CH_3COOC_2H_5 + H_2O$$

Reactive distillation is a process wherein the reaction vessel also functions as a still and a separate distillation step is not required. The use of reactive distillation in an equilibrium limited reaction such as esterification can increase the conversion rates by continuously removing reaction products. Benefits associated with using reactive distillation include increased speed, greater cost efficiency, reduced wastes and improved product quality.

Dehydrogenation of ethanol is an alternative method for the production of ethyl acetate from ethanol. Dehydrogenation is a chemical reaction that involves passing ethanol over a catalyst at high temperatures to eliminate hydrogen. The primary reaction has the following stoichiometry; $2C_2H_5OH \rightarrow C_4H_8O_2 + 2H_2$. An exemplary catalyst used in dehydrogenation processes is copper or copper-chromite, and the reaction requires temperatures of around 200-300°. A person skilled in the art would understand that dehydrogenation reactions using different catalysts at varying temperatures could also be used.

In certain aspects of the invention the process for the conversion of an alcohol and an acid to an ester, involves removal of the ester from the reaction chamber by a distillation process, in which the temperature of the reaction broth is raised, and the ester is removed, resulting in a waste stream. The resulting waste stream comprising predominantly water and being substantially free of the ester product. The waste stream can be returned to one or more bioreactors as at least a portion of the water required in the media composition.

EXAMPLES

CO Fermentation

Materials and Methods:

| Solution A | |
|---|---|
| NH₄Ac | 3.083 g |
| MgCl₂•6H₂O | 0.4 g |
| CaCl₂•2H₂O | 0.294 g |
| KCl | 0.15 g |
| NaCl (optional) | 0.12 g |
| Distilled Water | Up to 1 L |

| Solution B | |
|---|---|
| Biotin | 20.0 mg |
| Folic acid | 20.0 mg |
| Pyridoxine•HCl | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Liter |

| Solution C | |
|---|---|
| Component | mmol/L H2O |
| FeCl₃ | 0.1 |
| CoCl₂ | 0.05 |
| NiCl₂ | 0.05 |
| H₃BO₃ | 0.01 |
| Na₂SeO₃ | 0.01 |
| Na₂MoO₄ | 0.01 |
| ZnCl₂ | 0.01 |
| MnCl2 | 0.01 |
| Na2WO3 | 0.01 |

Preparation of Cr (II) Solution

A 1 L three necked flask was fitted with a gas tight inlet and outlet to allow working under inert gas and subsequent transfer of the desired product into a suitable storage flask. The flask was charged with $CrCl_3.6H_2O$ (40 g, 0.15 mol), zinc granules [20 mesh] (18.3 g, 0.28 mol), mercury (13.55 g, 1 mL, 0.0676 mol) and 500 mL of distilled water. Following flushing with $N_2$ for one hour, the mixture was warmed to about 80° C. to initiate the reaction. Following two hours of stirring under a constant $N_2$ flow, the mixture was cooled to room temperature and continuously stirred for another 48 hours by which time the reaction mixture had turned to a deep blue solution. The solution was transferred into $N_2$ purged serum bottles and stored in the fridge for future use.

Bacteria:

*Clostridium autoethanogenum* deposited at the German Resource Centre for Biological Material (DSMZ) and allocated the accession numbers DSM 23693 was used for this experiment. The address of the German Resource Centre for Biological Material (DSMZ) is DSMZ GmbH Inhoffenstraβe, 7 B, D-38124 Braunschweig, Germany. The microorganism was deposited on 7 Jun. 2010.

Sampling and Analytical Procedures

Media samples were taken from the CSTR reactor at intervals over the course of each fermentation. Each time the media was sampled care was taken to ensure that no gas was allowed to enter into or escape from the reactor.

HPLC:

HPLC System Agilent 1100 Series. Mobile Phase: 0.0025N Sulfuric Acid. Flow and pressure: 0.800 mL/min. Column. Alltech IOA; Catalog #9648, 150×6.5 mm, particle size 5 μm. Temperature of column: 60° C. Detector: Refractive Index. Temperature of detector: 45° C.

Method for Sample Preparation:

400 μL of sample and 50 μL of 0.15M $ZnSO_4$ and 50 μL of 0.15M $Ba(OH)_2$ are loaded into an Eppendorf tube. The tubes are centrifuged for 10 min. at 12,000 rpm, 4° C. 200 μL of the supernatant are transferred into an HPLC vial, and 5 μL are injected into the HPLC instrument.

Headspace Analysis:

Measurements were carried out on a Varian CP-4900 micro GC with two installed channels. Channel 1 was a 10 m Molsieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Cell Density:

Cell density was determined by counting bacterial cells in a defined aliquot of fermentation broth. Alternatively, the absorbance of the samples was measured at 600 nm (spectrophotometer) and the dry mass determined via calculation according to published procedures.

Example 1

Batch Fermentation in CSTR

Approximately 1500 mL of solution A was transferred into a 1.5 L fermenter and sparged with nitrogen. Resazurin (1.5 mL of a 2 g/L solution) and $H_3PO_4$ (85% solution, 2.25 mL) was added and the pH adjusted to 5.3 using concentrated $NH_4OH(aq)$. Nitrilotriacetic acid (0.3 ml of a 0.15M solution) was added prior to 1.5 ml of solution C. $Na_2WO_3$ (1.5 mL of a 0.01M solution) was added. 15 ml of Solution B was added and the solution sparged with $N_2$ before switching to CO containing gas (50% CO; 50% N2) at 60 mL/min. The fermenter was then inoculated with 180 ml of a *Clostridium autoethanogenum* 23693 culture. The fermenter was maintained at 37° C. and stirred at 300 rpm. During this experiment, $Na_2S$ solution (0.5M solution) was added at a rate of approximately 0.12 ml/hour. Substrate supply was increased in response to the requirements of the microbial culture.

Figure 5:
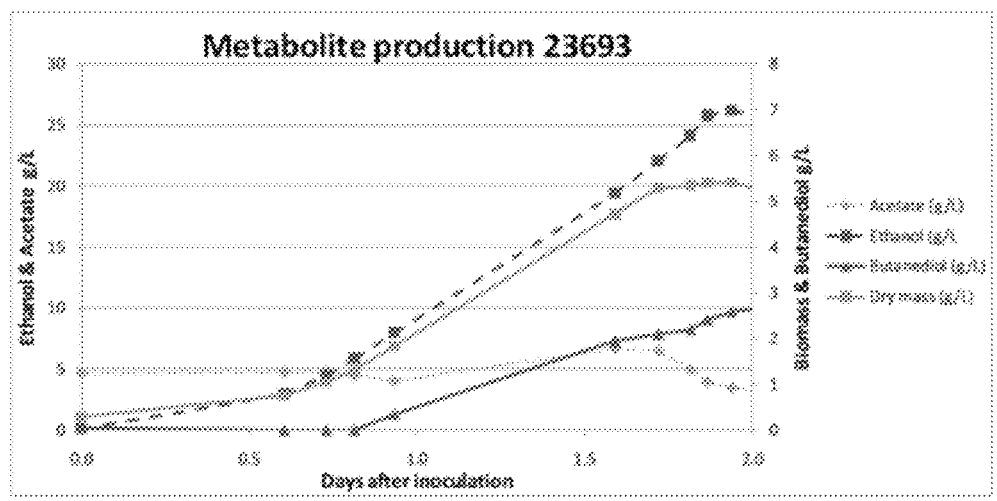
FIG. 5 is a graphical representation showing metabolite production by anaerobic fermentation in accordance with methods of the present invention.

The bacterial culture proliferated in the experimental conditions used. The culture showed a 8400 mM CO uptake after 43 hrs of growth (Figure while the doubling time of the culture was 9.6 hrs (FIG. 5). This corresponds to a specific growth rate of 1.73 $day^{-1}$. The maximum specific CO uptake reached during the experiment was 1.17 mMol CO/min/g biomass. Day 1.0 specific uptake: 1.17 mM CO/min/g biomass (Table 1). Day 2.0 specific uptake: 1.03 mM CO/min/g biomass (Table 2).

Results:

TABLE 1

| Day 1 | |
|---|---|
| | DSM23693 |
| CO consumption mM/L | 3700 mM |
| Ethanol Production g/L | 7.98 g/L |

TABLE 1-continued

Day 1

| | DSM23693 |
|---|---|
| Acetate Production g/L | 4.06 g/L |
| Biomass g/L | 1.83 g/L |
| Specific uptake | 1.17 CO/min/g biomass |
| Specific ethanol production | 4.3 g/L/g biomass/day |

TABLE 2

Day 2

| | DSM23693 |
|---|---|
| CO consumption mM/L | 8150 mM |
| Ethanol Production g/L | 26.14 g/L |
| Acetate Production g/L | 3.47 g/L |
| Biomass g/L | 5.42 g/l |
| Specific uptake | 1.03 CO/min/g biomass |
| Specific ethanol production | 6.5 g/L/g biomass/day |

Example 2

Approximately 1500 mL of solution A was transferred into a 1.5 L fermenter and sparged with nitrogen. Resazurin (1.5 mL of a 2 g/L solution) and $H_3PO_4$ (85% solution, 0.56 mL) was added and the pH adjusted to 5.3 using concentrated $NH_4OH(aq)$. Solution C (1.5 mL) was added after which $Na_2WO_3$ (1.5 mL of a 0.01M solution) was added. 15 ml of Solution B was added and the solution sparged with N2 before switching to CO containing gas (50% CO; 50% N2) at 60 mL/min. The fermenter was then inoculated with 100 ml of a *Clostridium autoethanogenum* 23693 culture. The fermenter was maintained at 37° C. and stirred at 300 rpm. During this experiment, Na2S solution (0.5M solution) was added at a rate of approx 0.15 ml/hour. Substrate supply was increased in response to the requirements of the microbial culture.

Figure 6:
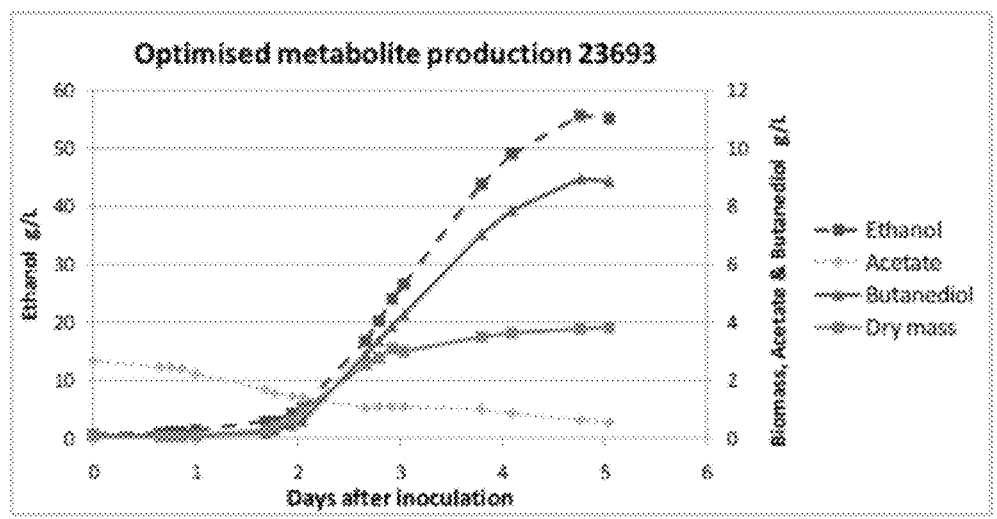
FIG. 6 is a graphical representation showing optimised metabolite production by anaerobic fermentation in accordance with methods of the present invention.

The bacterial culture proliferated in the experimental conditions used. The fermentation conditions were identical or at least highly similar to the conditions used in Example 1 while both gasses contained CO at least 50% (v/v). As shown in FIG. 6 the culture was grown to the stationary phase where maximum ethanol concentration was measured by HPLC (55.8 g/L).

EXAMPLES

CO2/H2 Fermentation

Materials and Methods
Media:

| Solution A - Concentration per 1 L of Media | |
|---|---|
| $MgCl_2$ | 0.05 g |
| NaCl | 1.2 g |
| $CaCl_2$ | 0.05 g |
| KCL | 0.15 g |
| 85% $H_3PO_4$ | 0.375 ml |
| Composite B vitamin solution | 10 ml |
| Composite trace metal solution | 10 ml |

-continued

| Resazurin (2000 mg/L stock) | 0.5 ml |
| Distilled Water | Up to 1 L |

| Solution B | |
|---|---|
| Biotin | 20.0 mg |
| Folic acid | 20.0 mg |
| Pyridoxine•HCl | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Liter |

| Solution C - | |
|---|---|
| Component | Per L H2O |
| $FeCl_3$ | 0.387 g |
| $CoCl_2$ | 0.0095 g |
| $NiCl_2$ | 0.027 g |
| $Na_2WO_4$ | 0.0132 g |
| $H_3BO_3$ | 0.0025 g |
| $Na_2SeO_3$ | 0.0069 g |
| $Na_2MoO_4$ | 0.0097 g |
| $ZnCl_2$ | 0.0136 g |
| $MnCl_2•4H_2O$ | 0.0097 g |

Media at pH 6.5 was prepared as follows. All ingredients of solution A were mixed in 1000 ml distilled water. The pH of this solution was adjusted to 6.5 with concentrated $(NH_4)OH$. After that, the media was degassed with N2

Bacteria:

*Acetobacterium woodii* were obtained from the German Resource Centre for Biological Material (DSMZ). The accession number given to the bacteria is DSM 1030.

Fermentation in Bioreactor:

A three-liter reactor was filled with 1500 ml of the media. Oxygen was removed from the media by continuously sparging with $N_2$. The gas was switched from $N_2$ to a mixture of 60% $H_2$, 20% $CO_2$, and 20% $N_2$ 30 minutes before inoculation. The inoculum (150 ml) came from a continuous *Acetobacterium woodii* culture fed with the same gas mixture. The bioreactor was maintained at 30° C. and stirred at 200 rpm at the time of inoculation. During the following batch growth phase, agitation was increased incrementally to 600 rpm. The gas flow was increased incrementally by 50 ml/min according to the dropping H2/CO2 in the headspace as a result of the increasing biomass. To compensate for the acetic acid produced, the pH was automatically controlled to 7 using 5 M NaOH. Throughout the fermentation, a 0.5M solution of Na2S was pumped into the fermenter at a rate of 0.2 ml/hour.

The culture was made continuous after 1 day. To reach high biomass along with high gas consumption, it is necessary to keep the acetate concentration in the fermenter at levels below 20 g/L. This was realized by running the fermenter at a relatively high dilution rate (D~1.7/day) while retaining the microbes in the fermenter with a polysulfon membrane filtration system with 0.1 μm pore size (GE healthcare hallow fibre membrane). The medium for the continuous culture was solution A excluding the composite trace metal solution, which was fed separately at a rate of 1.5 ml/hour using an automated syringe pump. The medium was degassed at least 1 day before and continuously degassing throughout fermentation process.

Sampling and Analytical Procedures:

Media samples were taken at intervals over a 30 day period

All samples were used to establish the absorbance at 600 nm (spectrophotometer) and the level of substrates and products (GC or HPLC). HPLC was routinely used to quantify the level of acetate, ethanol.

Headspace of fermenter was analysed automatically by Gas-GC (Varian 4900 Micro-GC) at hourly.

Results

Acetic acid in a continuous culture was demonstrated at a concentration of approximately 17.76 g/L (296 mM). The productivity of acetate reached 21.8 g/L/day. Table 3 demonstrates acetic acid productivity of approximately 70 g/L/day by fermentation of CO2 and H2 by *A. woodii*. Table 3 further show $H_2$ and $CO_2$ uptake by during the fermentation.

TABLE 3

| $H_2$ mol/L day | $CO_2$ mol/L/day | Acetic acid g/L/day |
|---|---|---|
| 4.9 | 2.27 | 60 |
| 5.8 | 2.58 | 71 |
| 5.5 | 2.5 | 70 |
| 5.27 | 2.38 | 65 |

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

We claim:
1. A method for the production of ethyl acetate, the method comprising:
   a. passing a gaseous substrate comprising CO to a bioreactor comprising a culture of a *Clostridium autoethanogenum* bacterium strain deposited at the German Collection of Microorganisms and Cell Cultures (DSMZ) under the accession number DSM 23693;
   b. anaerobically fermenting the substrate comprising CO to produce a fermentation broth comprising ethanol;
   c. passing the fermentation broth to an extraction module, wherein the ethanol is separated from the fermentation broth to provide a purified ethanol stream and a waste broth stream;
   d. passing the waste broth stream back to the bioreactor;
   e. passing the purified ethanol stream to a reaction vessel; and
   f. converting the purified ethanol to ethyl acetate in the reaction vessel by a process selected from esterification or dehydrogenation.

2. The method of claim 1 further comprising continuously removing water produced as a by-product of the esterification reaction from the reaction vessel by reactive distillation.

3. The method of claim 1 wherein hydrogen is produced as a by-product of the dehydrogenation reaction in the reaction vessel and the hydrogen is recovered.

4. The method of claim 3 wherein the recovered hydrogen is recycled back to the bioreactor for use as a co-substrate in the fermentation reaction.

5. The method of claim 1 wherein the gaseous substrate comprising CO is derived from a process selected from the group consisting of steam reforming, water gas shift, ferrous metal products manufacturing, non-ferrous products manufacturing, petroleum refining processes, gasification of coal, electric power production, carbon black production, ammonia production, methanol production, gasification of coal and coke manufacturing.

\* \* \* \* \*